United States Patent
Blood et al.

(10) Patent No.: US 11,851,518 B2
(45) Date of Patent: Dec. 26, 2023

(54) SEPARATIONS SYSTEM FOR RECOVERING HYDROCARBONS FROM SYNTHESIS OF POLYETHYLENE POLYMERS

(71) Applicant: Dow Global Technologies LLC, Midland, MI (US)

(72) Inventors: Mark W. Blood, S. Charleston, WV (US); Brent J. Sherman, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 528 days.

(21) Appl. No.: 16/973,075

(22) PCT Filed: Jun. 12, 2019

(86) PCT No.: PCT/US2019/036703
§ 371 (c)(1),
(2) Date: Dec. 8, 2020

(87) PCT Pub. No.: WO2019/241341
PCT Pub. Date: Dec. 19, 2019

(65) Prior Publication Data
US 2021/0246234 A1 Aug. 12, 2021

Related U.S. Application Data

(60) Provisional application No. 62/685,403, filed on Jun. 15, 2018.

(51) Int. Cl.
*C07C 7/00* (2006.01)
*B01D 3/14* (2006.01)
(Continued)

(52) U.S. Cl.
CPC .............. *C08F 6/005* (2013.01); *B01D 3/148* (2013.01); *B01D 3/322* (2013.01); *B01J 19/24* (2013.01);
(Continued)

(58) Field of Classification Search
CPC .......... B01D 3/00; B01D 3/322; B01D 3/148; C08F 2/01; C08F 2/34; C08F 6/005; C07C 7/00; C07C 9/18; C07C 9/14
See application file for complete search history.

(56) References Cited

U.S. PATENT DOCUMENTS 4,885,063 A 12/1989 Andre et al.
5,533,437 A 7/1996 Howard et al.
(Continued)

FOREIGN PATENT DOCUMENTS

EP 3093070 11/2016
RU 2475297 C2 2/2013
(Continued)

OTHER PUBLICATIONS

International Preliminary Report on Patentability for related PCT Application PCT/US2019/036703, dated Dec. 24, 2020 (7 pgs).
(Continued)

*Primary Examiner* — Rip A Lee
(74) *Attorney, Agent, or Firm* — Brooks, Cameron & Huebsch PLLC

(57) ABSTRACT

The present disclosure provides for a separations system for separating ethylene, 2-methylbutane and at least one unsubstituted (C6-C12) hydrocarbon in a multi-component condensate mixture. The separations system includes a feed conduit in fluid communication with a source of the multi-component condensate mixture, a stripper column in fluid communication with the feed conduit, where the stripper column separates the multi-component condensate mixture
(Continued)

into a heavies component mixture with at least one unsubstituted (C6-C12) hydrocarbon, and a top mixture having a medium component (s) that include at least the 2-methylbutane and a light component (s) that include at least the ethylene. The separations system further includes a flash drum that separates the top mixture into the medium component (s) and the light component (s). The separations system does not include a distillation column disposed between the source of the multi-component condensate mixture and the flash drum.

12 Claims, 2 Drawing Sheets

(51) Int. Cl.
  *B01D 3/32* (2006.01)
  *C08F 6/00* (2006.01)
  *B01J 19/24* (2006.01)
  *C07C 7/04* (2006.01)
  *C07C 7/09* (2006.01)
(52) U.S. Cl.
  CPC ............... *C07C 7/005* (2013.01); *C07C 7/04* (2013.01); *C07C 7/09* (2013.01)

(56) References Cited

U.S. PATENT DOCUMENTS

| | | |
|---|---|---|
| 5,741,350 A | 4/1998 | Rowles et al. |
| 6,107,533 A | 8/2000 | Vebeliunas et al. |
| 7,524,904 B2 | 4/2009 | Verser et al. |
| 8,017,701 B2 | 9/2011 | Mcelvain et al. |
| 8,362,161 B2 | 1/2013 | Mills et al. |
| 9,273,169 B2 | 3/2016 | Schrick et al. |
| 9,540,467 B2 | 1/2017 | Marissal et al. |
| 10,793,494 B2 * | 10/2020 | Asprion .................. B01D 3/40 |
| 11,021,553 B2 * | 6/2021 | Chen ........................ C07C 2/34 |
| 2005/0038207 A1 | 2/2005 | Burns et al. |
| 2008/0234448 A1 | 9/2008 | Pratt |
| 2013/0125581 A1 | 5/2013 | Force et al. |
| 2015/0329445 A1 | 11/2015 | Kleiber et al. |

FOREIGN PATENT DOCUMENTS

| | | | | |
|---|---|---|---|---|
| WO | WO 2004/024311 A1 * | 3/2004 | ............... | B01J 8/00 |
| WO | WO 2014/091015 A1 * | 6/2014 | ............... | C07C 7/04 |

OTHER PUBLICATIONS

International Search Report & Written Opinion for related PCT Application PCT/US2019/036703, dated Oct. 2, 2019 (10 pgs).

* cited by examiner

SEPARATIONS SYSTEM FOR RECOVERING HYDROCARBONS FROM SYNTHESIS OF POLYETHYLENE POLYMERS

This application is a National Stage Application under 35 U.S.C. § 371 of International Application Number PCT/US2019/036703, filed Jun. 12, 2019 and published as WO 2019/241341 on Dec. 19, 2019, which claims the benefit to U.S. Provisional Application 62/685,403, filed Jun. 15, 2018, the entire contents of which are incorporated herein by reference in its entirety

TECHNICAL FIELD

Separation system for recovering hydrocarbons, particularly for recovering monomers and condensing agent used in gas phase synthesizing of polyethylene polymers and oligomers made thereby.

BACKGROUND

Olefins, such as ethylene, may be polymerized by contacting them under polymerization conditions with a catalyst to produce a granular polymer. Straight from the polymerization reactor, the granular polymers contain gases such as unreacted olefin monomers as well as other hydrocarbons used and/or produced during the polymerization process. These gases are removed from the granular polymer in the form of "vent gases" for many reasons including, for example, recovering the unreacted olefin monomers and inert condensing agents, for quality control of the polymer product and for safety reasons. As such, recovering and properly handling the vent gases from the granular polymers is an important step in the process of olefin polymer production.

There are various techniques for removing and processing vent gases from granular polymers. For example, a purge process utilizing a polymer purge bin, or product purge bin, is a common process used to remove vent gases, such as alkenes, from the granular polymers. The purging process generally comprises conveying the granular polymer to a polymer purge bin and contacting the granular polymer in the purge bin with an inert purge gas stream to strip away the vent gases from the granular polymers. Nitrogen is most commonly used as the inert purge gas. However, it is also possible to use a light hydrocarbon rich gas to strip the heavier hydrocarbons in a first stage and then use an inert gas in a second stage for stripping the light hydrocarbons that remain in and around the granular polymer after the first stage.

A vent recovery system is then typically utilized to recover hydrocarbons, such as unreacted olefin monomers, from the vent gases and inert purge gas stream exiting the purge bin. Existing methods of recovering hydrocarbons from the vent gases include: (a) compression and condensation with at least one of water or air, mechanical refrigeration, and ethylene expansion; and (b) separation via pressure swing absorption or membranes. In existing gas phase polyethylene plants, option (a) is most commonly used, however, a combination of option (a) and option (b) may also be used.

In a compression and condensation system, the vent gases containing the inert gas, such as nitrogen, the olefin monomers and other hydrocarbons are treated in a series of steps that include: (a) cooling to condense a portion of the vent gases; (b) separating the condensed liquids from the remaining non-condensable light gases; (c) compressing the non-condensable light gases; (d) cooling the compressed stream to promote further condensing; (e) further separating the condensed liquids from the remaining non-condensable light gases; and (f) recycling the condensed liquids containing the olefin monomer.

Conventional compression and cooling vent recovery systems using ambient air or water cooling may recover most of the heavier hydrocarbons, such as 1-butene, 1-methylbutane (iso-pentane), 1-hexene, hexane, octane, decane, dodecane, and other heavy alkanes and olefins, contained in the vent gases. However, the amount of hydrocarbon recovery is constrained by the practical limit on the ambient cooling medium supply temperature. Furthermore, the inert gas, such as nitrogen, remaining in the vent gases after the condensed liquid separation, may still contain significant amounts of heavier hydrocarbons, precluding its re-use as a resin drying or purge gas. To reach a higher level of olefin monomer recovery and achieve a higher quality of recovered gas, further processing is required. To this end, refrigeration systems including mechanical refrigeration and olefin expansion, may also be used for cooling vent gases. Refrigeration systems have certain advantages over conventional ambient cooling, such as the ability to achieve a final condensation temperature of below 0° C., and thus may be more efficient in hydrocarbon removal from vent gases. However, a significant amount of ethylene may remain in the non-condensed vent gases.

Therefore, there still exists a need for an improved system and method for separating olefin monomers from other hydrocarbons in vent gases that would help to recover and use more of the olefin monomer and inert condensing agents from vent gases (thereby reducing flaring of unrecovered hydrocarbons) and allow the re-use of vent gases containing inert gases, such as nitrogen ($N_2$).

SUMMARY

The present disclosure provides for a separation system and a method for separating olefin monomers from inert condensing agents in vent gases recovered from a product purge bin of a gas phase reactor process. The separation system and the method of the present disclosure can separate the olefin monomers from the inert condensing agents without the use of a distillation column. Instead, the separation system and the method of the present disclosure utilize both a stripper column and a flash drum in conjunction with compression stages that help to further extract and separate olefin monomers from inert condensing agents in vent gases recovered from a product purge bin of a gas phase reactor process.

Specifically, the present disclosure provides for a separations system for separating ethylene, 2-methylbutane and at least one unsubstituted ($C_6$-$C_{12}$) hydrocarbon in a multi-component condensate mixture having 2-methylbutane, ethylene, fines and at least one unsubstituted ($C_6$-$C_{12}$) hydrocarbon, the separations system including: a feed conduit in fluid communication with a source of the multi-component condensate mixture; a stripper column in fluid communication with the feed conduit, the stripper column having a top portion, a bottom portion distal from the top portion and three to ten theoretical stages, the stripper column configured to receive through the feed conduit the multi-component condensate mixture at a temperature in a range of −13 degrees Celsius (° C.) to −5° C. and a pressure of 340 kilopascals (kPag) to 420 kPag, wherein the stripper column is further configured for operating at an internal pressure of 200 kPa to 1500 kPa to separate the multi-component condensate mixture into: a heavies component mixture with the at least one unsubstituted ($C_6$-$C_{12}$) hydrocarbon, and a top mixture having a medium component(s) and a light component(s), wherein the medium component(s) include at least the 2-methylbutane and the light component(s) include at least the ethylene, wherein the top portion of the stripper column is configured to remove the top mixture and the bottom portion of the stripper column is configured to remove the heavies component mixture; a reboiler in fluid communication with the stripper column, the reboiler configured for operating at a temperature of 50° C. to 200° C.; a condenser in fluid communication with the top portion of the stripper column, wherein the condenser is configured to cool the top mixture coming from the top portion of the stripper column to a temperature of −19° C. to 42° C.; and a flash drum having a top portion and a bottom portion distal from the top portion, wherein the flash drum is in fluid communication with the condenser to receive the top mixture having been cooled from the condenser, the flash drum configured for operating at a temperature of −19° C. to 70° C. and a pressure of 240 kPa to 405 kPa to separate the top mixture into the medium component(s) and the light component(s), wherein the top portion of the flash drum is configured to remove the light component(s) of the top mixture and wherein the bottom portion of the flash drum is configured to remove the medium component(s) of the top mixture, with the proviso that for the separations system there is no distillation column disposed between the source of the multi-component condensate mixture and the flash drum.

The present disclosure also includes a gas phase polymerization system that includes a gas phase polymerization reactor; a product purge bin in sequential fluid communication with the gas phase polymerization reactor; and the separations system as described herein in sequential fluid communication with the product purge bin and the gas phase polymerization reactor, wherein the light component(s) containing at least the ethylene from the top portion of the flash drum are returned to the gas phase polymerization reactor.

The present disclosure also includes a method of separating ethylene, 2-methylbutane and at least one unsubstituted ($C_6$-$C_{12}$) hydrocarbon in a multi-component condensate mixture having 2-methylbutane, ethylene, fines and at least one unsubstituted ($C_6$-$C_{12}$) hydrocarbon, where the method includes feeding the multi-component condensate mixture at a temperature in a range of −13 degrees Celsius (° C.) to −5° C. and a pressure of 340 kilopascals (kPag) to 420 kPag into a stripper column having a top portion, a bottom portion distal from the top portion and three to ten theoretical stages, the stripper column operating at an internal pressure of 200 kPa to 1500 kPa; separating the multi-component condensate mixture with the stripper column into a heavies component mixture with the at least one unsubstituted ($C_6$-$C_{12}$) hydrocarbon, and a top mixture having medium component(s) and a light component(s), wherein the medium component(s) include at least the 2-methylbutane and the light component(s) include at least the ethylene, removing the top mixture from the top portion of the stripper column and the heavies component mixture from the bottom portion of the stripper column; cooling the top mixture to a temperature of −19° C. to 42° C.; and separating the top mixture cooled to the temperature of −19° C. to 42° C. into the medium component(s) and the light component(s) in a flash drum having a top portion and a bottom portion distal from the top portion, wherein the flash drum operates at a temperature of 15° C. to 70° C. and a pressure of 240 kPa to 405 kPa to separate the top mixture into the medium component(s) and the light component(s), wherein the light component(s) are removed from the top portion of the flash drum and the medium component(s) are removed from the bottom portion of the flash drum with the proviso that the method does not use a distillation column between the source of the multi-component condensate mixture and the flash drum.

DETAILED DESCRIPTION

Figure 1:
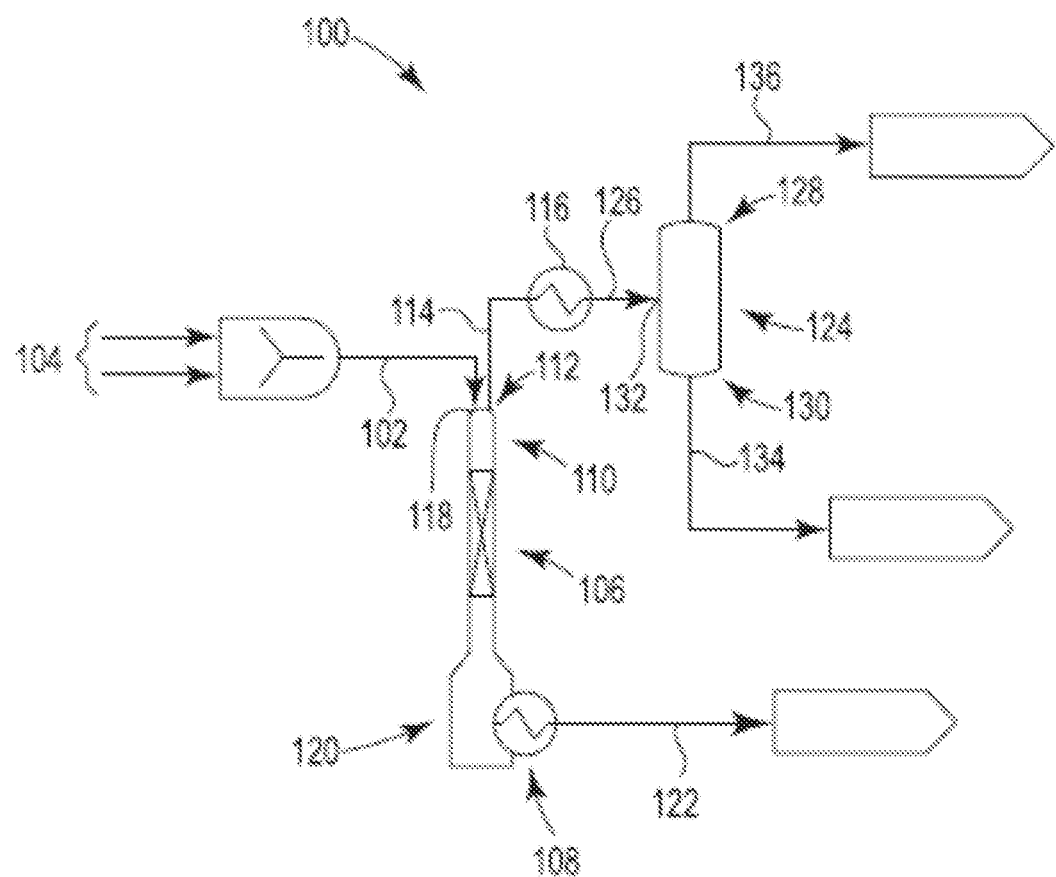
FIG. 1 illustrates an embodiment of a separations system according to the present disclosure.

The present disclosure provides for a separation system and a method for separating olefin monomers from inert condensing agents in vent gases recovered from a product purge bin of a gas phase polymerization system. The separation system and the method of the present disclosure can separate the olefin monomers from the inert condensing agents without the use of a distillation column. Instead, the separation system and the method of the present disclosure utilize both a stripper column and flash drum in conjunction with compression stages that help to further extract and separate olefin monomers from inert condensing agents in vent gases recovered from the product purge bin of the gas phase polymerization system.

Unless defined otherwise herein, chemical engineering terms are based on *Perry's Chemical Engineer's Handbook* (6th ed.) and *Separation Process Principles* by Seader, Henley, and Roper (3rd ed.). Stripper column, a vessel that encloses a stripping mass transfer process. The stripper column of the present disclosure performs reboiled stripping, as opposed to gas stripping or refluxed stripping, which is gas stripping but with reflux. Stripping, the selective removal of components by mass transfer from the liquid phase to the gas phase without the use of external reflux. Reboiler, a heat exchanger used to generate vapor by heating the liquid at the bottom of a column and returning the generated vapor back to the column. Reboiling, the act of generating stripping vapor by heating the liquid at the bottom of a column and returning the generated vapor back to the column. Flash drum, a vessel designed to separate a liquid phase from a vapor phase as a consequence of a temperature and/or pressure change occurring either upstream or inside of the vessel. Flashing, the act of a liquid-vapor mixture reaching a new equilibrium state through the separation of a liquid and vapor phase. Distillation column, also referred to as a fractionation column, a vessel that is designed to enclose a distillation mass transfer process. Distilling, the act of separating through stripping and rectification a feed mixture of two or more components into two or more products including at a minimum an overhead distillate and a bottoms product, where the products have a different composition from the feed mixture. The stripper column is distinguished from a distillation column by virtue of the fact that the stripper column does not have and is not connected to, and its method of use does not include, external reflux, except for the case of gas stripping with reflux. The flash drum is distinguished from the stripper column and from the distillation column by virtue of the fact that the flash drum provides only one new equilibrium state, whereas the stripper column provides multiple new equilibrium states and the distillation column provides multiple new equilibrium states.

Specifically, embodiments of the present disclosure provide a separations system for separating ethylene, 2-methylbutane (iso-pentane) and at least one unsubstituted ($C_6$-$C_{12}$) hydrocarbon in a multi-component condensate mixture having 2-methylbutane, ethylene, fines and at least one unsubstituted ($C_6$-$C_{12}$) hydrocarbon. The at least one unsubstituted ($C_6$-$C_{12}$) hydrocarbon can be a normal ($C_6$-$C_{12}$) alkane selected from hexane, octane, decane, and dodecane; and, optionally, an alpha-olefin selected from 1-butene, 1-hexene, and 1-octene. The multi-component condensate mixture may further comprise propene and at least one normal-($C_5$-$C_{11}$)alkane selected from pentane, heptane, nonane, and undecane. Alternatively, the multi-component condensate mixture may be free of propene and at least one normal-($C_5$-$C_{11}$)alkane selected from pentane, heptane, nonane, and undecane; alternatively, free of a cyclic ($C_3$-$C_{12}$) hydrocarbon; alternatively, free of propene, pentane, heptane, nonane, undecane, and a cyclic ($C_3$-$C_{12}$) hydrocarbon.

With most catalyst systems used in the reactor, all the liquid condensed in vent recovery is returned to the reactor. However, newly developed catalyst systems used in making bi-modal polyethylene resins use larger alkanes such as iso-octane to feed the catalyst system in slurry to the gas phase polymerization reactor. The new catalysts, however, can produce small amounts of heavier hydrocarbons, such as $C_{10}$ and $C_{12}$ hydrocarbons. These heavier compounds are condensed in the various stages of vent recovery and are sent back to the reactor with the olefin monomers and inert condensing agents. The return of these heavy hydrocarbons to the reactor, however, causes operating difficulties. The current way to prevent excessive build-up of these heavy hydrocarbons in the reactor is to discard part of the liquid recovered in vent recovery. This discarding of the vent recovery liquids results in the loss of the some of the recovered monomer and induced condensing agent, with most of the loss being the condensing agent, thus creating an operating cost increase. The embodiments of the present disclosure address these and other issues as discussed herein.

In the interest of clarity, certain pumps, heat exchangers, control valves, control systems, and auxiliary equipment items for the practical and safe operation of the systems discussed herein, but which are not necessary to illuminate the inventive concepts, have been left out of the drawings. One skilled in the art understands that the deleted equipment is included in practical and safe operating units. Accordingly, the deletions do not limit the scope of the disclosure.

The figures herein follow a numbering convention in which the first digit or digits correspond to the drawing figure number and the remaining digits identify an element in the drawing. Similar elements between different figures may be identified by using similar digits. For example, 354 may reference element "54" in FIG. 3, and a similar element may be referenced as 454 in FIG. 4. It is emphasized that the purpose of the figures is to illustrate, and the figures are not intended to be limiting in any way. The figures herein may not be to scale and relationships of elements in the figures may be exaggerated. The figures are employed to illustrate conceptual structures and methods herein described.

Referring to FIG. 1, there is shown an embodiment of a separation system 100 according to the present disclosure. The separation system 100 allows for the separation of ethylene, 2-methylbutane and at least one unsubstituted ($C_6$-$C_{12}$) hydrocarbon in a multi-component condensate mixture having 2-methylbutane, ethylene, fines and at least one unsubstituted ($C_6$-$C_{12}$) hydrocarbon, as discussed herein. The separation system 100 includes a feed conduit 102 in fluid communication with a source 104 of the multi-component condensate mixture. The separation system 100 further includes a stripper column 106 with a reboiler 108, where the stripper column 106 is in fluid communication with the feed conduit 102. The stripper column 106 further includes a top portion 110 having a top exit 112 that provides a fluid connection through top conduit 114 to a condenser 116.

The stripper column 106 further includes a top inlet 118 in fluid connection with the feed conduit 102, where the feed conduit 102 supplies the multi-component condensate mixture to the separation system 100. As discussed herein, the multi-component condensate mixture can be a mixture of hydrocarbons and purge media (e.g., nitrogen), where the mixture of hydrocarbons can include, but are not limited to, an olefin monomer (e.g., ethylene), an inert condensing agent (e.g., 2-methylbutane), olefin co-monomer different than the olefin monomer (e.g., n-hexene) and larger unsubstituted hydrocarbons such as, for example, n-hexane, n-octane, iso-octane, n-decane and n-dodecane, among others as discussed herein. The stripper column 106 is configured to receive through the feed conduit 102 the multi-component condensate mixture at a temperature in a range of −13 degrees Celsius (° C.) to −5° C. and a pressure of 340 kilopascals gauge (kPag) to 420 kPag, as discussed herein.

The stripper column 106 further includes a bottom portion 120 distal from the top portion 110, where the bottom portion 120 includes the reboiler 108. The reboiler 108 forms a vapor stream from the components of the multi-component condensate mixture in the bottom portion 120 of the stripper column 106 to act as the stripping agent in the stripper column 106. In the stripper column 106, the vapor stream from the components of the multi-component condensate mixture coming from the reboiler 108 helps to separate the multi-component condensate mixture into a heavies component mixture and a top mixture, as is discussed herein.

The stripper column 106 as shown in FIG. 1 operates with a countercurrent flow, where the liquid of the multi-component condensate mixture enters the top portion 110 of the stripper column 106 through the top inlet 118 and the vapor stream is generated by the reboiler 108. In one embodiment, the reboiler 108 can be a stab-in bundle type reboiler. Other types of reboilers are possible. The stripper column 106 is sized and configured to have three to ten theoretical stages. Preferably, the stripper column 106 is sized and configured to have six to eight theoretical stages. The stages in the stripper column 106 can be formed with packing or with trays. Preferably, the stripper column 106 is a packed column. For the various embodiments, the packing can be a random packing or a structured packing, as are known in the art. Examples of packing materials include Raschig rings, Berl saddles, Pall rings, Zbigniew Bialecki rings and Intalox saddles, among others.

The stripper column 106 can have a diameter of fifteen (15) centimeters (cm) to about ninety-one (91) cm and a height of six (6) meters (m) to thirteen (13) m. The reboiler 108 of the stripper column 106 operates at a temperature of 50° C. to 200° C. to provide for a pressure inside the stripper column 106 of 200 kPa to 1500 kPa. Preferably, the reboiler 108 of the stripper column 106 operates at a temperature of 110° C. to 200° C. In a preferred embodiment, the stripper column 106 operates at a pressure that is as close as possible to the pressure generated in a second compression stage of a multi-stage compressor as will be discussed more fully herein. Pressure inside the stripper column 106 can be controlled by the backpressure of the top mixture leaving the top exit 112 of the stripper column 106 using a back pressure regulating control valve. The temperature inside the stripper column 106 can be from 50° C. to 200° C. All individual values and subranges of temperatures from 50° C. to 200° C. are included and disclosed herein; for example, the temperature can be from a lower value of 50, 55, 60 and 65° C. to an upper value of 130, 150, 180 and 200° C. Preferably, the stripper column 106 operates at a temperature of 60° C. to 180° C., and most preferably the stripper column 106 operates at a temperature of 68° C. to 150° C. Similarly, all individual values and subranges of pressures from 200 kPa to 1500 kPa are included and disclosed herein; for example, the pressure can be from a lower value of 200, 300, 400 and 500 kPa to an upper value of 800, 900, 1100 and 1500 kPa. Preferably, the stripper column 106 operates at a pressure of 300 kPa to 500 kPa, and most preferably the stripper column 106 operates at a pressure of 350 kPa to 400 kPa. Preferably, the stripper column 106 operates at a pressure that is close to or slightly below the pressure of the multi-component condensate mixture entering the stripper column 106 through the feed conduit 102. For the various embodiments, the stripper column 106 can be operated with a molar boil-up ratio of 15 to 30.

As noted herein, the reboiler 108 can be a stab-in reboiler heated by steam or another suitable heating medium, but it can be any other suitable type of heat exchanger such as a thermosyphon or a multi-pass shell and tube heat exchanger as the design and size of the stripper column 106 dictates. Preferably, the reboiler 104 of the stripper column 106 operates to provide a temperature and pressure inside the stripper column 106 to separate the top mixture from the heavies component mixture and drive the top mixture to exit the stripper column 106 through the top exit 112 as a vapor. Optionally (not shown in FIG. 1), the stripper column 106 can be equipped with an external reboiler.

Once inside the stripper column 106, the multi-component condensate mixture separates into the heavies component mixture and the top mixture. The heavies component mixture includes at least one unsubstituted $C_6$, $C_8$, $C_{10}$ or $C_{12}$ hydrocarbon. The heavies component mixture is removed from the separation system 100 by conduit 122, where it can be sent for other subsequent processing or to a flare. Many of these hydrocarbons are formed in side reactions during polyolefin gas phase reactor process. The separation system and method of the present disclosure can be adapted readily for use with various gas phase polymerization reactors and methods such as those mentioned in WO2006026493A1, WO2007075615A2, WO2015022025A1, US20080234448A1, U.S. Pat. No. 9,745,389B2, and U.S. Pat. No. 9,790,293B2.

The stripper column 106 also separates the multi-component condensate mixture into the top mixture, where the top mixture includes both a medium component(s) and a light component(s). For the various embodiments, the medium component(s) include at least the inert condensing agent (e.g., 2-methylbutane), and the light component(s) includes at least the olefin monomers (e.g., ethylene). For example, when used in gas phase reactor processes, as discussed herein, the medium component(s) include at least 2-methylbutane while the light component(s) include at least ethylene monomers.

The separation system 100 further includes the condenser 116 in fluid communication with the top portion 110 of the stripper column 106. As illustrated, the condenser 116 is in fluid communication with the top portion 110 of the stripper column 106 through conduit 114 by way of the top exit 112. Condenser 116 is configured to cool the top mixture coming from the top portion 110 of the stripper column 106 to a temperature of −19° C. to 42° C. The condenser 116 can be sized to ensure its capacity to transfer heat from the top mixture is sufficient for the required cooling load. The condenser 116 can be of a shell-and-tube or an air-fin design cooled with water or a refrigerant. Other types of condensers are also possible.

As illustrated in FIG. 1, the separation system 100 further includes a flash drum 124, where the flash drum 124 is in fluid communication with the condenser 116 via conduit 126 to receive the top mixture having been cooled from the condenser 116. The flash drum 124 includes a top portion 128 and a bottom portion 130 distal from the top portion 128. The flash drum 124 includes a feed inlet 132 connected to the condenser 116 via conduit 126. The feed inlet 132 also includes a throttling value that regulates a pressure drop of the top mixture coming from the condenser 116. As the top mixture enters the flash drum 124 the top mixture separates into the medium component(s) and the light component(s). As previously noted, the light component(s) include the olefin monomers from the vent gases coming from the polymerization process, where these components of the top mixture are more volatile than the inert condensing agent from the polymerization process. The flash drum 124 receives the top mixture directly from the top portion 110 of the stripper column 106 via the condenser 116 and separates the top mixture into the medium component(s) and the light component(s). The medium component(s) are removed as a bottom stream through bottom conduit 134 from the flash drum 124, and the light component(s) are removed as a top stream through top conduit 136 from the flash drum 124. As the medium component(s) contains mostly the inert condensing agent(s) (e.g., 2-methylbutane), it can be returned to the gas phase polymerization system for further use. Similarly, as the light component(s) includes at least the olefin monomer (e.g., ethylene), it can either be returned to the gas phase polymerization system (e.g., the vent recovery system) for further use or undergo further separation to increase the concentration of the olefin monomer.

For the various embodiments provided herein, the flash drum 124 operates in an essentially isothermal mode at a temperature of 15° C. to 70° C. and a pressure of 240 kPa to 405 kPa. All individual values and subranges of temperatures from 15° C. to 70° C. are included and disclosed herein; for example, the temperature can be from a lower value of 15° C., 20° C., 25° C. and 30° C. to an upper value of 45° C., 55° C., 65° C. and 70° C. Preferably, the flash drum 124 operates at a temperature of 25° C. to 55° C., and most preferably the flash drum 124 operates at a temperature of 30° C. to 40° C. Similarly, all individual values and subranges of pressures from 240 kPa to 405 kPa are included and disclosed herein; for example, the pressure can be from a lower value of 350 kPa, 360 kPa, 370 kPa, and 375 kPa to an upper value of 380 kPa, 385 kPa, 395 kPa and 405 kPa. Preferably, the flash drum 124 operates at a pressure of 360 kPa to 380 kPa, and most preferably the flash drum 124 operates at a pressure of 370 kPa to 375 kPa. In various embodiments, the flash drum 124 of the present disclosure can be jacketed to allow for heat exchange fluid (e.g., water or a refrigerant) to help control the temperature inside the volume of the flash drum 124. The flash drum 124 can be configured vertically or horizontally as desired. The flash drum may contain internals comprised of baffles or demisters to ensure adequate vapor-liquid separation.

As discussed herein, the feed conduit 102 supplies the multi-component condensate mixture to the stripping column 106 of the separation system 100 through the top inlet 118. For the various embodiments, the stripper column 106 receives the multi-component condensate mixture through the feed conduit 102 at a temperature in a range of −13° C. to −5° C. and a pressure of 340 kPag to 420 kPag. All individual values and subranges of temperatures from −13° C. to −5° C. are included and disclosed herein; for example, the temperature can be from a lower value of −13° C., −11° C., −10° C. and −9° C. to an upper value of −8° C., −7° C., −6° C. and −5° C. Preferably, the stripper column 106 receives the multi-component condensate mixture at a temperature of −12° C. to −9° C., and most preferably the stripper column 106 receives the multi-component condensate mixture at a temperature of −11° C. to −10° C. Similarly, all individual values and subranges of pressures from 340 kPag to 420 kPag are included and disclosed herein; for example, the pressure can be from a lower value of 340 kPag, 350 kPag, 360 kPag and 370 kPag to an upper value of 380 kPag, 390 kPag, 400 kPag and 420 kPag. Preferably, the stripper column 106 receives the multi-component condensate mixture at a pressure of 380 kPag to 420 kPag, and most preferably the stripper column 106 receives the multi-component condensate mixture at a pressure of 410 kPag to 420 kPag.

Figure 2:
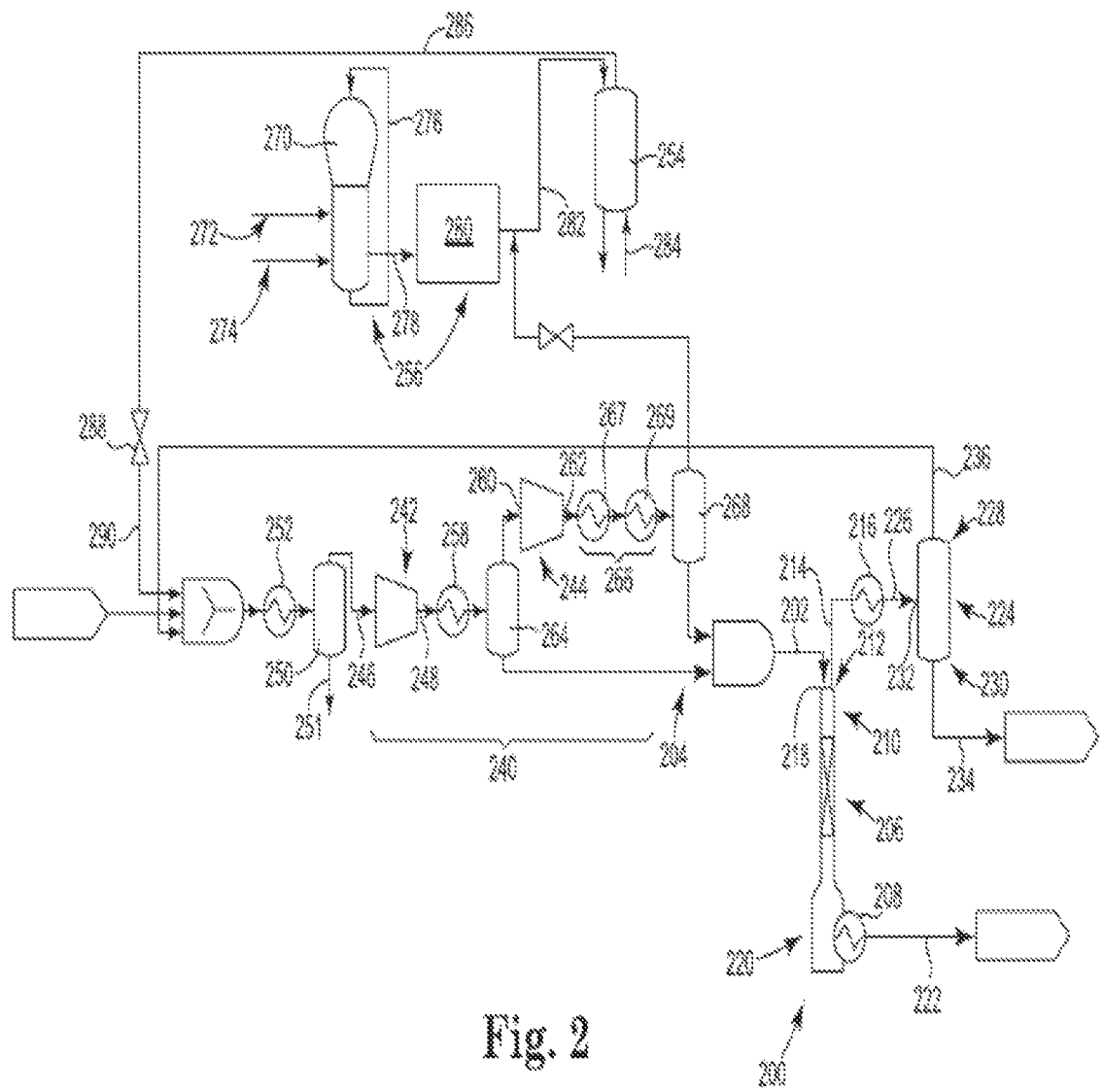
FIG. 2 illustrates an embodiment of a gas-phase polymerization system with the separations system according to the present disclosure.

To achieve the desired temperature and pressure for the multi-component condensate mixture the separations system of the present disclosure can further include a multi-stage compressor. As seen in FIG. 2, the separations system 200 is shown with a multi-stage compressor 240 that includes a first compression stage 242 and a second compression stage 244. The separation system 200 includes the stripper column 206 having the reboiler 208, the flash drum 224 and associated components as previously described for FIG. 1, which will not be repeated here.

Referring to FIG. 2, the first compression stage 242 has a gas phase inlet 246 and a gas phase outlet 248, where the gas phase inlet 246 is in fluid communication with a first accumulator 250. The first accumulator 250 is in fluid communication with a first condenser system 252 and a product purge bin 254 of a gas phase polymerization system 256. The gas phase outlet 248 of the first compression stage 242 is in fluid communication with a second condenser system 258. The second compression stage 224 has a gas phase inlet 260 and a gas phase outlet 262, where the gas phase inlet 260 in fluid communication with a second accumulator 264. The second accumulator 264 is in fluid communication with the second condenser system 258 and the gas phase outlet 262 is in fluid communication with a third condenser system 266 that is in fluid communication with a third accumulator 268.

The first condenser system 252 receives and cools vent gases from polymer granules in the product purge bin 254 of the gas phase polymerization system 256 to a temperature of −10° C. to 60° C. at a pressure of 110 kPag to 150 kPag to produce a first gas mixture. As discussed herein, vent gases are separated from the polymer granules by passing a purge medium through the product purge bin 254. The purge medium may be an inert gas, such as nitrogen or argon, or any gas low in the hydrocarbons that are targeted for removal from the polymer granules, for example, an olefin monomer. Polymerization reaction effluent frequently contains unreacted olefin monomer entrained with the polymerization granules. The vent gases may include monomers and co-monomers, such as $C_2$ to $C_{12}$ olefins and dienes; reactor diluents, such as $C_1$ to $C_{10}$ hydrocarbons; and an inert, such as nitrogen or argon. In some embodiments, the vent gases include ethylene monomer. The vent gases may also include $C_4$ to $C_{12}$ co-monomers. The vent gases may also include reaction by-products such as linear $C_6$, $C_8$, $C_{10}$ and/or $C_{12}$ hydrocarbons, which can be detrimental to the polymerization reaction if returned to the gas phase polymerization system 256. The vent gases may also include an inert condensing agent, such as, for example, a cycloalkane, 2-methylpropane, 2-methylbutane, and n-hexane, may be used to raise the molecular weight or specific heat of the vent gases to promote condensation of the lighter component(s), such as ethylene monomer.

FIG. 2 also provides an illustration of the gas phase polymerization system 256 that includes a gas phase polymerization reactor 270 having a catalyst feed line 272 and an olefin monomer feed line 274, which supply catalyst and olefin monomers, respectively, to the gas phase polymerization reactor 270. The gas phase polymerization reactor 270 further includes recycle stream 276 to recycle unreacted reactor components (e.g., olefin monomers) back to the gas phase polymerization reactor 270. Polymer granules along with some reactor gases are withdrawn from the gas phase polymerization reactor 270 through conduit 278 and conducted to a product chamber 280. The reactor contents pass through product chamber 280 and are conveyed through conduit 282 and, optionally a product blow tank (not illustrated) to a product purge bin 254, allowing the product purge bin to be in sequential fluid communication with the gas phase polymerization reactor 270. Within the product purge bin 254 the polymer granules are separated from the reactor gases. The polymer granules are purged with an inert gas, as discussed herein, fed through line 284 and the resulting vent gases are fed through conduit 286 and valve 288 into a product conveying line 290. As seen in FIG. 2, the separations system 200 is in sequential fluid communication with the product purge bin 254 and the gas phase polymerization reactor 270. As discussed herein, the light component(s) containing at least the ethylene from the top portion 228 of the flash drum 224 are returned to the gas phase polymerization reactor 270.

The vent gases in the product conveying line 290 are then directed to the first condenser system 252, which receives and cools the vent gases from polymer granules in the product purge bin 254 of the gas phase polymerization system 256 to a temperature of −10° C. to 60° C. at a pressure of 110 kPag to 150 kPag to produce a first gas mixture and a purge condensate. The purge condensate includes the heavier component mixture with the at least one substituted $C_6$, $C_8$, $C_{10}$ or $C_{12}$ hydrocarbon from the vent gases. The purge condensate can also include other hydrocarbons, such as n-butene and 2-methylpropane among other hydrocarbons. The purge condensate is removed via conduit 251 from the separation system to be flared or for further processing.

In contrast to the first condensate, the first gas mixture passes through the first accumulator 250 into the gas phase inlet 246 of the first compression stage 242, where the first compression stage 242 compresses the first gas mixture to a pressure of 375 kPag to 404 kPag and a temperature of 100° C. to 150° C. The second condenser system 258 receives and cools the first gas mixture from the gas phase outlet 248 of the first compression stage 242 to a temperature of −10 to 60° C. at a pressure of 375 kPag to 404 kPag. The first gas mixture from the second condenser system 258 then enters the second accumulator 264. A second gas mixture and a first condensate are produced in the second accumulator 264.

The second gas mixture passes through the second accumulator 264 to the gas phase inlet 260 of the second compression stage 244, where the second compression stage 244 compresses the second gas mixture to a pressure of 1300 kPag to 10300 kPag. The third condenser system 266 receives and cools the second gas mixture from the gas phase outlet 262 of the second compression stage 244 to a temperature of −10 to 60° C. at a pressure of 1300 kPag to 10300 kPag. The second gas mixture enters the third accumulator 268, which produces both a recycle gas mixture and a second condensate. The third accumulator 268 is in fluid communication with the gas phase polymerization system so as to allow the recycle gas mixture, being rich in the inert purge gas (e.g., nitrogen), to be returned to the gas phase polymerization system 256 to help convey the polymer granules from the gas phase polymerization reactor 270 to the product purge bin 254.

The first compression stage 242 and the second compression stage 244 can each be a centrifugal compressor, a reciprocating compressor or a screw compressor. One skilled in the art would recognize that other types of compressors could also be used. For the various embodiments, the first condenser system 252, the second condenser system 258 and the third condenser system 266 can be cooled with ambient air, cooling water or with refrigeration (e.g., mechanical refrigeration). In addition to the system shown in FIG. 2, those with ordinary skill in the art will recognize that additional compressors, liquid/gas separators, heat exchangers etc. can be added to the above system. The third condenser system 266 provides an example of the use of two condensers in series, where each condenser can be cooled in the same or a different matter. For example, as seen in FIG. 2 the third condenser system 266 can include a water-cooled condenser 267 in sequential fluid communication with a refrigerated condenser 269.

For the various embodiments, the first condensate produced in the second accumulator 264 is fed to the stripper column 206 via the feed conduit 202 is at least part of the source of the multi-component condensate mixture. In an additional embodiment, both the first condensate produced in the second accumulator 264 and the second condensate produced in the third accumulator 268 are fed to the stripper column 206 via the feed conduit 202 as at least part of the source of the multi-component condensate mixture. As discussed herein, the stripper column 206 receives the multi-component condensate mixture at a temperature in a range of −13° C. to −5° C. and a pressure of 340 kPag to 420 kPag via feed conduit 202.

Other optional elements and components that can be included with the separation system 100, 200 include the addition of a second flash drum after flash drum 124, 224, where the top conduit 136, 236 from the flash drum 124, 224 is introduced into the second flash drum at a temperature and pressure to allow for further recovery of the olefin monomer. This second flash drum could be cooled by mechanical refrigeration to allow for an operating temperature of no greater than about 17° C. to help with recovering the olefin monomer. It is also envisioned to include a single stage compressor positioned along conduit 126, 226 to the flash drum 124, 224 to allow for the top mixture coming from the stripper 106, 206 to achieve a pressure of at least 900 kPag to help with recovering olefin monomer.

Each of the embodiments of the separation system (e.g., 100 and 200) provided herein include the proviso that there is no distillation column disposed between the source of the multi-component condensate mixture (e.g., 104, 204) and the flash drum (e.g., 124 or 224). This provides the advantage of a reduced number of components for achieving the desired separation discussed herein with its associated reduction in costs for both the construction and operation of the separation system 100, 200 provided herein.

The present disclosure also provides for a method of separating ethylene from iso-pentane in the multi-component condensate mixture using the separations system provided herein for and described in any one of FIG. 1 and/or FIG. 2. As noted herein, the separations system 100, 200 does not include a distillation column. Rather, the method of the present disclosure allows for separating ethylene, 2-methylbutane and at least one unsubstituted ($C_6$-$C_{12}$) hydrocarbon in the multi-component condensate mixture having 2-methylbutane, ethylene, fines and at least one unsubstituted ($C_6$-$C_{12}$) hydrocarbon using the separation system 100, 200 discussed herein. The method includes feeding the multi-component condensate mixture at a temperature in a range of −13° C. to −5° C. and a pressure of 340 kPag to 420 kPag into the stripper column 106, 206 having the top portion 110, 210, the bottom portion 120, 220 distal from the top portion 110, 210 and the three to ten theoretical stages as discussed herein. As previously noted herein, the stripper column 106, 206 operates at an internal pressure of 200 kPa to 1500 kPa. The multi-component condensate mixture is separated with the stripper column 106, 206 into the heavies component mixture with the at least one unsubstituted ($C_6$-$C_{12}$) hydrocarbon, and the top mixture having a medium component(s) and a light component(s), as discussed herein, where the medium component(s) include at least the 2-methylbutane and the light component(s) include at least the ethylene. The top mixture is removed from the top portion 110, 210 of the stripper column 106, 206 and the heavies component mixture from the bottom portion 120, 220 of the stripper column 106, 206. The top mixture is cooled to a temperature of −19° C. to 42° C. and then the top mixture cooled to the temperature of −19° C. to 42° C. is separated into the medium component(s) and the light component(s) in the flash drum 124, 224 having the top portion 128, 228 and the bottom portion 130, 230 distal from the top portion 128, 228. As discussed herein, the flash drum operates at a temperature of 15° C. to 70° C. and a pressure of 240 kPa to 405 kPa to separate the top mixture into the medium component(s) and the light component(s). The light component(s) are removed from the top portion 128, 228 of the flash drum 124, 224 and the medium component(s) are removed from the bottom portion 130, 230 of the flash drum 124, 224 with the proviso, as noted above, that the system and method of the present disclosure does not use a distillation column between the source of the multi-component condensate mixture and the flash drum 124, 224.

The method can further include at least one of item (i), (ii), (iii) and/or (iv), where (i) includes feeding the medium component(s) exiting from the bottom portion 130, 230 of the flash drum 124, 224 into a gas phase polymerization reactor 270; (ii) includes feeding the light component(s) exiting from the top portion 128, 228 of the flash drum 124, 224 into the gas phase polymerization reactor 270; (iii) includes operating the stripper column 106, 206 with no external reflux; and (iv) includes operating the flash drum 106, 206 at a temperature of −19° C. to 70° C.

The method can further include at least one of item (i), (ii) and/or (iii): where (i) includes producing with the separations system 200 the multi-component condensate mixture at least partially from vent gases from polymer granules in the product purge bin 254 of the gas phase polymerization system 256; (ii) includes conveying polymer granules from the gas phase polymerization reactor 270 to a product purge bin 254 using the recycle gas mixture produced in the separation system 200 that includes the multi-stage compressor 240; and (iii) includes filtering the multi-component condensate mixture to remove the fines from the multi-component condensate mixture, as discussed herein.

The method may further include at least one of item (i), (ii) and/or (iii): where (i) includes feeding the light component(s) removed from the top portion 128, 228 of the flash drum 124, 224 into a compressor configured and operative for compressing ethylene; (ii) includes flashing the light component(s) from the top portion 128, 228 of the flash drum 124, 224 in a second flash drum; (iii) includes compressing the top mixture from the top portion 110, 210 of the stripper column 106, 206 prior to cooling the top mixture to the temperature of −19° C. to 42° C.; and (iv) includes compressing the light component(s) from the top stream of the flash drum 124, 224 prior to flashing the light component(s) from the top stream of the flash drum 124, 224 in a second flash drum.

What is claimed is:

1. A separations system for separating ethylene, 2-methylbutane and at least one unsubstituted ($C_6$-$C_{12}$) hydrocarbon in a multi-component condensate mixture having 2-methylbutane, ethylene, fines and at least one unsubstituted ($C_6$-$C_{12}$) hydrocarbon, the separations system comprising:
    a feed conduit in fluid communication with a source of the multi-component condensate mixture;
    a stripper column in fluid communication with the feed conduit, the stripper column having a top portion, a bottom portion distal from the top portion and three to ten theoretical stages, the stripper column configured to receive through the feed conduit the multi-component condensate mixture at a temperature in a range of −13 degrees Celsius (° C.) to −5° C. and a pressure of 340 kilopascals gauge (kPag) to 420 kPag, wherein the stripper column is further configured for operating at an internal pressure of 200 kPa to 1500 kPa to separate the multi-component condensate mixture into:
        a heavies component mixture with the at least one unsubstituted ($C_6$-$C_{12}$) hydrocarbon, and
        a top mixture having a medium component(s) and a light component(s), wherein the medium component(s) include at least the 2-methylbutane and the light component(s) include at least the ethylene, wherein the top portion of the stripper column is configured to remove the top mixture and the bottom portion of the stripper column is configured to remove the heavies component mixture;
    a reboiler in fluid communication with the stripper column, the reboiler configured for operating at a temperature of 50° C. to 200° C.;
    a condenser in fluid communication with the top portion of the stripper column, wherein the condenser is configured to cool the top mixture coming from the top portion of the stripper column to a temperature of −19° C. to 42° C.; and
    a flash drum having a top portion and a bottom portion distal from the top portion, wherein the flash drum is in fluid communication with the condenser to receive the top mixture having been cooled from the condenser, the flash drum configured for operating at a temperature of 15° C. to 70° C. and a pressure of 240 kPa to 405 kPa to separate the top mixture into the medium component(s) and the light component(s), wherein the top portion of the flash drum is configured to remove the light component(s) of the top mixture and wherein the bottom portion of the flash drum is configured to remove the medium component(s) of the top mixture, with the proviso that there is no distillation column disposed between the source of the multi-component condensate mixture and the flash drum.

2. The separations system of claim 1, further including a multi-stage compressor having a first compression stage and a second compression stage, wherein
    the first compression stage has a gas phase inlet and a gas phase outlet, the gas phase inlet in fluid communication with a first accumulator, wherein the first accumulator is in fluid communication with a first condenser system and a product purge bin of a gas phase polymerization system, and wherein the gas phase outlet is in fluid communication with a second condenser system; and
    the second compression stage has a gas phase inlet and a gas phase outlet, the gas phase inlet in fluid communication with a second accumulator, wherein the second accumulator is in fluid communication with the second condenser system, and wherein the gas phase outlet is in fluid communication with a third condenser system that is in fluid communication with a third accumulator;
    wherein the first condenser system is configured to receive and cool vent gases from polymer granules in the product purge bin of the gas phase polymerization system to a temperature of −10 to 60° C. at a pressure of 110 kPag to 150 kPag to produce a first gas mixture, wherein the first gas mixture passes through the first accumulator into the gas phase inlet of the first compression stage, the first compression stage configured to compress the first gas mixture to a pressure of 375 kPag to 404 kPag and a temperature of 100° C. to 150° C.;
    wherein the second condenser system is configured to receive and cool the first gas mixture from the gas phase outlet of the first compression stage to a temperature of −10 to 60° C. at a pressure of 375 kPag to 404 kPag and configured to produce a second gas mixture and a first condensate in the second accumulator;
    wherein the second gas mixture passes through the second accumulator to the gas phase inlet of the second compression stage, wherein the second compression stage is configured to compress the second gas mixture to a pressure of 1300 kPag to 10300 kPag;
    wherein the third condenser system is configured to receive and cool the second gas mixture from the gas phase outlet of the second compression stage to a temperature of −10 to 60° C. at a pressure of 1300 kPag to 10300 kPag and configured to produce a recycle gas mixture and a second condensate in the third accumulator.

3. The separations system of claim 2, wherein the third accumulator is in fluid communication with the gas phase polymerization system to allow the recycle gas mixture to help convey the polymer granules from the gas phase polymerization system to the product purge bin.

4. The separations system of claim 3, wherein the first condensate is at least part of the source of the multi-component condensate mixture.

5. The separations system of claim 4, wherein the first condensate and the second condensate are at least part of the source of the multi-component condensate mixture.

6. The separations system of claim 2, wherein the third condenser system includes a water-cooled condenser in sequential fluid communication with a refrigerated condenser.

7. The separations system of claim 1, wherein packing inside the stripper column forms the three to ten theoretical stages of the stripper column.

8. A gas phase polymerization system, comprising:
a gas phase polymerization reactor;
a product purge bin in sequential fluid communication with the gas phase polymerization reactor; and
the separations system of claim 1 in sequential fluid communication with the product purge bin and the gas phase polymerization reactor, wherein the light component(s) include at least the ethylene from the top portion of the flash drum are returned to the gas phase polymerization reactor.

9. A method of separating ethylene, 2-methylbutane and at least one unsubstituted ($C_6$-$C_{12}$) hydrocarbon in a multi-component condensate mixture having 2-methylbutane, ethylene, fines and at least one unsubstituted ($C_6$-$C_{12}$) hydrocarbon, the method comprising:
feeding the multi-component condensate mixture at a temperature in a range of −13 degrees Celsius (° C.) to −5° C. and a pressure of 340 kilopascals (kPag) to 420 kPag into a stripper column having a top portion, a bottom portion distal from the top portion and three to ten theoretical stages, the stripper column operating at an internal pressure of 200 kPa to 1500 kPa;
separating the multi-component condensate mixture with the stripper column into a heavies component mixture with the at least one unsubstituted ($C_6$-$C_{12}$) hydrocarbon, and a top mixture having a medium component(s) and a light component(s), wherein the medium component(s) include at least the 2-methylbutane and the light component(s) include at least the ethylene,
removing the top mixture from the top portion of the stripper column and the heavies component mixture from the bottom portion of the stripper column;
cooling the top mixture to a temperature of −19° C. to 42° C.; and
separating the top mixture cooled to the temperature of −19° C. to 42° C. into the medium component(s) and the light component(s) in a flash drum having a top portion and a bottom portion distal from the top portion, wherein the flash drum operates at a temperature of 15° C. to 70° C. and a pressure of 240 kPa to 405 kPa to separate the top mixture into the medium component(s) and the light component(s), wherein the light component(s) are removed from the top portion of the flash drum and the medium component(s) are removed from the bottom portion of the flash drum with the proviso that the method does not use a distillation column between the source of the multi-component condensate mixture and the flash drum.

10. The method of claim 9, further comprising at least one of item (i), (ii), (iii) and/or (iv):
(i) feeding the medium component(s) exiting from the bottom portion of the flash drum into a gas phase polymerization reactor;
(ii) feeding the light component(s) exiting from the top portion of the flash drum into the gas phase polymerization reactor;
(iii) operating the stripper column with no external reflux
(iv) operating the flash drum at a temperature of −19° C. to 70° C.

11. The method of claim 10, further comprising at least one of item (i), (ii) and/or (iii):
(i) producing the multi-component condensate mixture at least partially from vent gases from polymer granules in a product purge bin;
(ii) conveying polymer granules from a gas phase polymerization reactor to a product purge bin using a recycled gas mixture;
(iii) filtering the multi-component condensate mixture to remove the fines from the multi-component condensate mixture.

12. The method of claim 11, further comprising at least one of item (i), (ii), (iii) and/or (iv):
(i) feeding the light component(s) removed from the top portion of the flash drum into a compressor configured and operative for compressing ethylene;
(ii) flashing the light component(s) from the top portion of the flash drum into a second flash drum;
(iii) compressing the top mixture from the top portion of the stripper column prior to cooling the top mixture to the temperature of −19° C. to 42° C.;
(iv) compressing the light component(s) from the top portion prior to flashing the light component(s) from the top portion of the flash drum in a second flash drum.

* * * * *